(12) United States Patent
Kretschmar et al.

(10) Patent No.: US 7,939,643 B2
(45) Date of Patent: *May 10, 2011

(54) PRODUCTION OF A VON WILLEBRAND FACTOR PREPARATION USING HYDROXYLAPATITE

(75) Inventors: Michael Kretschmar, Seligenstadt (DE); Wolfgang Moeller, Oberusel (DE)

(73) Assignee: Biotest AG, Drgigich (DE)

( * ) Notice: Subject to any disclaimer, the term of this patent is extended or adjusted under 35 U.S.C. 154(b) by 842 days.

This patent is subject to a terminal disclaimer.

(21) Appl. No.: 10/594,455

(22) PCT Filed: Sep. 9, 2005

(86) PCT No.: PCT/EP2005/009728
§ 371 (c)(1),
(2), (4) Date: Jun. 22, 2007

(87) PCT Pub. No.: WO2006/029773
PCT Pub. Date: Mar. 23, 2006

(65) Prior Publication Data
US 2007/0299250 A1     Dec. 27, 2007

(30) Foreign Application Priority Data

Sep. 14, 2004  (DE) .................. 10 2004 044 419

(51) Int. Cl.
*A23J 1/00* (2006.01)
*C07K 17/00* (2006.01)
(52) U.S. Cl. ...................... 530/413; 530/350
(58) Field of Classification Search .................. None
See application file for complete search history.

(56) References Cited

U.S. PATENT DOCUMENTS

| | | | |
|---|---|---|---|
| 4,341,764 A | 7/1982 | Wallace et al. | |
| 4,774,323 A | 9/1988 | Newman et al. | |
| 4,789,733 A | 12/1988 | Winkelman et al. | |
| 5,128,245 A | 7/1992 | Greenberg et al. | |
| 5,408,039 A | 4/1995 | Burnouf-Radosevich et al. | |
| 5,441,635 A * | 8/1995 | Ichitsuka et al. | 210/198.2 |
| 5,710,254 A * | 1/1998 | Newman et al. | 530/383 |
| 6,465,624 B1 | 10/2002 | Fischer et al. | |
| 2007/0135619 A1 | 6/2007 | Kretschmar et al. | |
| 2007/0203330 A1 | 8/2007 | Kretschmar et al. | |

OTHER PUBLICATIONS

Mumby et al., Interactions of Thrombospondin with Extracellular Matrix Proteins: Selective Binding to Type V Collagen, The Journal of Cell Biology, 1984, vol. 98, pp. 646-652.*

Labrou, Design and selection of ligands for affinity chromatography, Journal of Chromatography B, 2003, vol. 790, pp. 67-78.*

Dumas et al., Crystal Structure of the Wild-type von Willebrand Facotor A1-Glycoprotien lbα Complex Reveals Conformation Differences with a Complex Bearing von Willebrand Disease Mutations, The Journal of Biological Chemistry, May 28, 2004, vol. 279, pp. 23327-23334.*

Zardi et al., Elution of fibronectin proteolytic fragments from a hydroxyapatitie chromatography column, Eur. J. Biochem., 1985, vol. 146, pp. 571-579.*

Schroder et al., Hydroxyapatite chromatography: altering the phosphate-dependent elution profile of protein as a function of pH, Analytical Biochemistry, 2003, vol. 313, pp. 176-178.*

Daniel Marshak (1996), Cold Spring Harbor Laboratory Press, Strategies for Protein Purification and Characterization: A Laboratory Course Manual, p. 58.*

Zykova T A et al., "A Simple and Effective Additional Step in Purification of Bovine Blood Serum Fibronectin", XP002352960, BIOSIS Database Accession No. PREV19847804777 (1983).

Barington, K. A. et al., "A Very High Purity Von Willebrand Factor Preparation Containing High Molecular Weight Multimers", Vox Sanguinis, vol. 76, pp. 85-89 (Mar. 1999).

Lethagen, S. et al., "A Comparative In Vitro Evaluation of Six Von Willebrand Factor Concentrates", Haemophilia, vol. 10, No. 3, pp. 243-249 (May 2004).

Burnouf-Radosevich, M. et al., "Chromatographic Preparation of a Therapeutic Highly Purified Von Willebrand Factor Concentrate from Human Cryoprecipitate", Vox Sanguinis, vol. 62, No. 1, pp. 1-11 (1992).

Veyradier, A. et al., "Laboratory Diagnosis of Von Willebrand Disease", vol. 28, No. 4, pp. 201-210 (Dec. 1998).

Federici, Augusto B., "The Factor VIII/von Willebrand Factor Complex: Basic and Clinical Issues", J. Hematology, vol. 88, suppl. 9, pp. 3-12 (May 2003).

Gorman, J. J. et al., "Studies on the Structure and Subunit Composition of Human Antihaemophilic Factor", Thrombosis Research, vol. 12, pp. 341-352 (1978).

Saundry, R. H. et al., "Chromatography of vWF on Dextran Sulphate Sepharose", Thrombosis Research, vol. 48, pp. 641-652 (1987).

Janson, J.C. et al. (editors), "Protein Purification: Principles, High Resolution Methods, and Applications", Second edition, Wiley-Liss, NY, pp. 190-191, 199-200 (1998).

Bernardi, Giorgio, "Chromatography of Proteins on Hydroxyapatite", Methods in Enzymology, vol. 27, pp. 471-479 (1973).

Written Opinion of the International Searching Authority issued in PCT/EP05/009728 (PCT/ISA/237).

* cited by examiner

*Primary Examiner* — Alexander D Kim
(74) *Attorney, Agent, or Firm* — Chalin Smith; Smith Patent Consulting, LLC

(57) ABSTRACT

This invention relates to a process for the production of a von Willebrand factor preparation, hydroxylapatite being used as a chromatography medium.

12 Claims, No Drawings

PRODUCTION OF A VON WILLEBRAND FACTOR PREPARATION USING HYDROXYLAPATITE

This application is a Rule 371 U.S. National Phase Filing of PCT/EP05/009728, filed Sep. 9, 2005, which, in turn, claims priority to German Patent Application No. 10 2004 044 419.6, filed Sep. 14, 2004, the contents of which are incorporated by reference herein in their entirety.

This invention relates to a process for the production of a von Willebrand factor preparation, hydroxylapatite being used as a chromatography medium.

The von Willebrand factor is a glycoprotein which is synthesized in endothelial cells and megakaryocytes. The molecular weight of the monomer is about 225,000 Da. Within the cell, the formation of disulfide bridges results in dimers which, in turn, associate into oligomers of up to 40 dimeric subunits, also via disulfide linkages. The concentration of the von Willebrand factor (VWF) released into the plasma is 5-10 mg/l.

In primary hemostasis, it is the object of VWF to arrange for the adhesion of thrombocytes to injured subendothelium and, under the conditions of high shear forces as in the arterial system, to support thrombocyte aggregation. As a function in secondary hemostasis, VWF binds factor VIII, an important cofactor in blood coagulation, in a non-covalent complex. Factor VIII is thus stabilized and protected against premature degradation.

The von Willebrand syndrome (VWS) is a bleeding disorder which is caused by a quantitative or qualitative change in VWF. Having a prevalence of 0.8-1.3%, VWS is the most frequently heritable bleeding disorder. In contrast to hemophilia A, men and women suffer equally therefrom. VWS is classified into different types: type 1 patients have a relatively low VWF level in the blood. Type 2 VWS combines all qualitative defects of VWS in the plasma. Disorders may occur in primary and/or secondary hemostasis. VWF lacks completely from type 3 patients. Some subtypes of type 2 and type 3 are referred to as a severe form of VWS. The severe form of VWS requires replacement therapies with VWF containing preparations.

Plasmatic factor VII preparations, which have a rather high VWF content, are often used to treat the severe form of VWS. Although, bleedings can be staunched by them, the thrombosis risk simultaneously increases, in particular in the case of frequent or prolonged use. This is due to an overdosage of factor VIII. The therapy of ill persons suffering from VWS with highly pure, factor VIII deficient or factor VIII free VWF concentrates is much more favorable in terms of patient safety.

Literature has described various processes for purifying and isolating VWF:

EP-A-0 416 983 discloses the isolation of a VWF factor VIII complex from human plasma by precipitation with a combination of barium chloride and aluminum hydroxide and the subsequent anion exchange chromatography on DEAE fractogel.

EP-0 469 985 represents a process in which VWF is isolated from cryoprecipitate using an anion exchanger. Here, factor VIII is bound at a salt concentration of 250 mM while VWF remains in the supernatant. Having lowered the salt concentration to 100-150 mM, the supernatant is bound to a second anion exchanger and eluted with 300-350 mM NaCl.

EP 0 503 991 describes the purification of VWF from human cryoprecipitate by a 3-stage process: 1. anion exchange chromatography with DEAE fractogel and elution of VWF by 0.15 M NaCl. 2. Re-chromatography on DEAE fractogel and elution of VWF by 0.17 M NaCl. 3. Separation of fibronectin and fibrinogen by gelatin sepharose affinity chromatography. VWF is here found in the flow. Solutions containing amino acids and calcium ions are used as buffers.

WO 89/12065 describes the separation of plasma proteins from plasma cryoprecipitates by binding the proteins to DEAE fractogel and step-wise elution by means of an increasing NaCl addition. The process is particularly suited to isolate factor VIII concentrates and to prepare concentrates of fibrinogen, fibronectin and VWF.

WO 96/10584 describes a process for isolating highly pure recombinant VWF by means of combined anion exchange/heparin affinity chromatography, and EP 0 705 846 discloses the isolation of high-molecular and low-molecular fractions of recombinant VWF by means of heparin affinity chromatography.

WO 98/38219 describes a process for isolating VWF, in which VWF is bound to a cation exchanger at a low salt concentration and VWF with high specific activity is isolated by fractional elution.

The processes described thus far are unfavorable. An anion exchange chromatography has an unsatisfactory resolution. A combination with affinity chromatography is usually necessary to isolate a highly pure preparation. Affinity chromatographies, in turn, are cost intensive. For a plasmatic VWF preparation, maximum specific activities of 83 U/mg protein were achieved in the combination of anion exchange and cation exchange chromatographies. Likewise, a specific activity of only 59.2 U/mg protein was achieved in a process in which anion exchange, immunoaffinity and cation exchange chromatographies were used for purifying a recombinant VWF.

It is an object of the present invention to provide a simple, effective production process with which a highly pure, substantially factor VIII free VWF preparation having a high specific activity can be produced in cost-effective manner.

It has been found surprisingly that a chromatography step with hydroxylapatite as chromatography matrix yields favorable results. It has been found surprisingly that hydroxylapatite cannot only be used as a binding chromatography where VWF is bound and the impurities remain unbound or are eluted in another stage but can also be used as flow chromatography where VWF passes through the column in unbound fashion and impurities are bound.

According to the invention hydroxylapatite is thus used as a flow chromatography medium for purifying VWF. The present invention relates to a process for purifying VWF, characterized by carrying out at least one hydroxylapatite chromatography where VWF is substantially unbound while contaminating proteins are absorbed to the chromatography medium.

Preferably less than 30%, more preferably less than 25%, even more preferably less than 20%, most preferably less than 10% of VWF present in the loading solution bind to the hydroxylapatite matrix.

Hydroxylapatite is a form of calcium phosphate having the composition $Ca_5(PO_4)_3OH$ or $Ca_{10}(PO_4)_6OH_2$ which can be used as a stationary phase for the chromatography of proteins, nucleic acids and other macromolecules. Along with the crystalline form of hydroxylapatite it is also possible to use a ceramic form which can be obtained by sintering. Hydroxylapatite can be bought from Bio-Rad (Munich, Germany), for example. Its ceramic hydroxylapatite is provided in two forms (type 1 and type 2). On account of larger surface areas, the type 1 material has a greater binding capacity for relatively small molecules, e.g. small proteins. In contrast, the particles of the type 2 material have larger pores which enable the penetration and thus better binding of large molecules, e.g. DNA or large proteins. These materials preferably have the following properties:

TABLE 1

| | Dynamic binding capacity | Nominal pore diameter |
|---|---|---|
| Type 1 | >13.7 mg lysozyme/ml CHT* | 600-800 Å |
| Type 2 | >6.8 mg lysozyme/ml CHT* | 800-1000 Å |

*CHT = ceramic hydroxylapatite

Crystalline or ceramic hydroxylapatite is freely available. Processes for the production thereof are known in the art.

The process according to the invention comprises that (i) a composition containing VWF and one or more contaminating proteins is contacted with a hydroxylapatite matrix so as to bind at least one contaminating protein to the hydroxylapatite matrix while VWF is not substantially bound to the hydroxylapatite matrix, and optionally thereafter (ii) unbound VWF is separated from the hydroxylapatite matrix. This embodiment is referred to as "flow chromatography" in the present application.

The process can be carried out as a column chromatography or batch process; it is preferred to carry it out as a column chromatography. In the case of column chromatography, VWF is in the flow and at least one contaminating protein, e.g. fibronectin and/or fibrinogen, is bound to hydroxylapatite.

According to this embodiment hydroxylapatite chromatography is carried out at a pH of 6.5 to 8.5, preferably 6.8 to 8.5, more preferably 6.8 to 7.5, most preferably 7.0 to 7.5. Running buffers, wash buffers and elution buffers and the protein solution to be applied usually have the same pH. However, variants are also practicable where these solutions have different pH values.

The VWF containing composition which is contacted with the hydroxylapatite matrix preferably contains sodium phosphate and/or potassium phosphate. The total concentration of sodium phosphate and/or potassium phosphate in the solution is e.g. 0 to 100 mM, preferably 10 to 50 mM, most preferably 20 to 40 mM, i.e. a buffer solution having said concentrations can be used as a running buffer.

The VWF containing solution, e.g. a previously purified cryoprecipitate solution, is applied to a hydroxylapatite column at a low salt concentration of 0-100 mM, preferably 10-50 mM, of potassium or sodium phosphate at a pH of preferably 6.8 to 8.5, more preferably at a pH of 7.0-7.5. The hydroxylapatite of this embodiment is preferably ceramic hydroxylapatite, more preferably of type 1, as sold by Bio-Rad (Munich, Germany). Under these conditions, the majority of VWF molecules does not bind to the matrix and is in the flow while the majority of the contaminating proteins, such as fibrinogen or fibronectin, bind to the matrix.

As a result of the flow chromatography according to the invention it is possible to obtain VWF preparations which only contain minor amounts of fibrinogen and fibronectin. The concentration of fibrinogen antigen in the flow fraction is usually below 25 µg/ml, preferably below 15 µg/ml, more preferably below 10 µg/ml, most preferably at most 5 µg/ml. The concentration of fibronectin antigen in the flow fraction is usually below 250 µg/ml, preferably below 150 µg/ml, more preferably below 100 µg/ml, most preferably at most 50 µg/ml. The concentration of fibrinogen antigen and fibronectin antigen can be determined by generally known processes, e.g. as described in the examples of the present application. The depletion of fibronectin and fibrinogen is recommended in particular because on account of their aggregation tendency these proteins may cause process engineering problems, e.g. in the case of filtrations. Fibronectin and fibrinogen in lyophilized end products often prevent the full solubility of a preparation.

If the loading solution contacted with the hydroxylapatite matrix contains fibrinogen and/or fibronectin (e.g. because it is a plasma fraction), a considerable depletion of the contaminating proteins fibrinogen and fibronectin can be achieved. For example, the fibrinogen concentration in the flow fraction is preferably below 10%, more preferably below 5%, even more preferably below 2.5% of the fibrinogen concentration in the loading solution (prior to flow chromatography). The fibronectin concentration in the flow fraction is preferably below 10%, more preferably below 5%, even more preferably below 2.5% of the fibronectin concentration in the loading solution (prior to flow chromatography).

The yield of flow chromatography (based on the mass balance) is usually above 50%, preferably above 60%, most preferably above 75%.

The specific activity (ristocetin cofactor activity per mg total protein) can be raised by flow chromatography by at least 100%, preferably by at least 150%, most preferably by at least 200%.

For the purpose of fine purification, VWF can be bound to a hydroxylapatite matrix and then be eluted. This form of application is referred to as "binding chromatography". Binding chromatography usually comprises that (a) VWF is bound to the hydroxylapatite matrix,
(b) contaminations are washed out at a lower salt concentration, and
(c) the VWF containing fraction of interest is subsequently eluted at a higher salt concentration.

In step (a), a solution containing VWF and one or more contaminating proteins are contacted with the hydroxylapatite matrix. The total concentration of sodium and/or potassium phosphate in this solution is usually 0 to 200 mM, preferably 1 to 100 mM, more preferably 1 to 50 mM, most preferably 10 to 30 mM.

In wash step (b), the hydroxylapatite matrix is washed with a buffer having a low salt concentration. The total concentration of sodium and/or potassium phosphate in this wash buffer is usually 100 to 300 mM, preferably 150 to 250 mM, most preferably 180 to 240 mM.

In step (c), the VWF containing fraction of interest can be eluted with a buffer having a relatively high salt concentration. The elution buffer usually contains 200 to 500 mM, preferably 250 to 400 mM sodium and/or potassium phosphate.

Yield and purity can be changed by changing the salt concentrations. The higher the salt concentration in the wash buffer, the cleaner the resulting fraction of interest. However, the yield is lowered by this. Furthermore, the selected pH value influences the optimum salt concentration for the wash buffer. The lower the pH, the stronger the binding of VWF to the hydroxylapatite matrix. Correspondingly, the selected salt concentrations can be higher with lower pH values and lower with higher pH values.

Binding hydroxylapatite chromatography is carried out at a pH of 5 to 7.5, preferably of 5.5 to below 6.8, most preferably of 6.0 to 6.5. Running, wash and elution buffers and the protein solution to be applied usually have the same pH. However, variants where these solutions have different pH values are also practicable.

In this form, the VWF containing solution, e.g. a previously purified cryopreciptate solution, is applied to a hydroxylapatite column, e.g. ceramic type 2 hydroxylapatite at a low salt concentration, preferably 0-100 mM, more preferably 10-30 mM, of potassium or sodium phosphate at a pH of 5.5-6.8, preferably 6.0-6.5. The majority of the VWF molecules are bound under these conditions. Contaminations, e.g. fibronectin, can be washed out by means of a solution at a higher salt concentration using e.g. potassium or sodium phosphate, e.g. 230 mM sodium phosphate, pH 6.0. The fraction of interest is then eluted with highly concentrated salt solutions, e.g. phosphate solutions, such as 400 mM sodium phosphate, pH 6.0, for example.

VWF preparations which are virtually free from detectable amounts of fibrinogen and fibronectin can be obtained by binding chromatography from the VWF fractions purified by means of flow chromatography. If the loading solution which is contacted with the hydroxylapatite matrix is a plasma fraction and/or contains fibrinogen or fibronectin, a virtually quantitative removal of the contaminating proteins, i.e. fibrinogen and fibronectin, from the solution can be achieved. Thus, the fibrinogen concentration in the elution fraction is preferably lower than 25% of the fibrinogen concentration in the loading solution (before the binding chromatography). The fibrinoectin concentration in the elution fraction is preferably lower than 10%, more preferably lower than 5%, of the fibronectin concentration in the loading solution (before the binding chromatography). The concentrations of fibrinogen and/or fibronectin in the elution fraction (fraction of interest) are usually below the detection limit of about 1 μg/ml.

VWF preparations having a high specific activity can be obtained by a binding chromatography carried out subsequent to the flow chromatography according to the invention. The specific activity in the elution fraction can be above 50 U/mg protein, preferably it is above 75 U/mg protein, more preferably above 85 U/mg protein, most preferably at least 100 U/mg protein. The VWF activity is determined by the ristocetin cofactor assay which identifies the binding capacity of VWF to the platelet receptor glycoprotein Ib/IX under the influence of the ristocetin antibiotic. The specific VWF activity can be determined as described in the examples.

For the production of a particularly pure VWF preparation it is possible to combine the hydroxylapatite flow chromatography according to the invention and the binding hydroxylapatite chromatography with each other or with other purification methods. As has turned out, it is particularly useful to initially carry out a flow chromatography with hydroxylapatite to deplete the main contaminations according to the above described process. Then, the fraction of interest is titrated with 1 M HCl to a pH of 6.0, for example. As described for binding chromatography, the sample is applied onto a hydroxylapatite column. VWF molecules are bound and eluted selectively.

In a particular embodiment, a flow chromatography with hydroxylapatite is initially carried out, VWF not binding to the hydroxylapatite matrix, and then the flow fraction is re-chromatographed under binding conditions and the VWF fraction is eluted.

The step yields are between 65% and 85%, which is very good with respect to the high purifying effectiveness. In connection with flow chromatography it is useful, but not necessary, to use phosphate ions as a buffer substance. Phosphate is a specific agent for the elution of VWF in the binding chromatography.

In a particular embodiment, it is possible to use fluoroapatite in place of pure hydroxylapatite as a chromatography matrix. Fluoroapatite is produced by reacting hydroxylapatite with a fluoride containing substance. The Bio-Rad company (Munich, Germany) produces e.g. ceramic fluoroapatite by a 90% conversion of ceramic hydroxylapatite with a fluorine reagent. As compared to hydroxylapatite, fluoroapatite is markedly more stable under acidic pH conditions. Therefore, fluoroapatite is usually used to carry out chromatographies at a pH lower than technically useful for hydroxylapatite. Regarding a purification of VWF molecules with fluoroapatite, the chromatography can be carried out in a way similar to the process proposed for hydroxylapatite. Salt concentrations have to be adapted to the selected pH value (>=5.0).

The process according to the invention can also comprise one or more of the following steps:
(1) quick-freezing at a temperature of below −30° C. and thawing near 0° C. (cryoprecipitation)
(2) ethanol precipitation or adsorption on aluminum hydroxide
(3) virus inactivation of the VWF containing composition by solvent/detergent treatment
(4) anion exchange chromatography
(5) precipitation of fibronectin by adjusting a pH to below pH 5.4
(6) affinity chromatography
(7) diafiltration or ultrafiltration
(8) rebuffering or dialysis or gel filtration
(9) sterile filtration
(10) lyophilization
(11) virus inactivation by heat treatment (e.g. about 30 min at about 100° C.)

Process steps (1) to (5) are preferably carried out prior to hydroxylapatite chromatography. However, it is also possible to carry out less than the 5 process steps. The sequence of the steps is not compulsory.

Steps (6) to (11) can be carried out, where desired. In particular, affinity chromatography is not necessary since a high purity can already be achieved by the hydroxylapatite chromatography.

Thus, a previously purified plasma fraction can be used as a starting material for the processes of the present invention. It may be a further purified cryoprecipitate solution. For example, the cryoprecipitate solution can be precipitated with aluminum hydroxide and/or be further purified chromatographically. Thus, the cryoprecipitate solution can be precipitated with aluminum hydroxide, for example, and then be further purified by means of anion exchange chromatography. It is also preferred for the cryoprecipitate solution to be subjected to virus inactivation. A preferred process for the virus inactivation is a solvent/detergent treatment as described in U.S. Pat. No. 4,540,573.

A protein solution containing recombinant VWF (rVWF) from cell culture supernatants can also be used as a starting material. The expression "rVWF" also covers variants having an amino acid sequence modified with respect to a wild-type VWF, wherein one or more amino acids may be substituted, deleted and/or added. The variants usually have VWF activity. Processes for the production of suitable expression vectors, for introducing the vectors into the host cells and for culturing the host cells are generally known to the person skilled in the art (Fischer et al., Structural analysis of recombinant von Willebrand factor: identification of hetero and homo-dimers. FEBS Lett 1994; 351:345-348. Fischer et al., Structural analysis of recombinant von Willebrand factor produced at industrial scale fermentation of transformed CHO cells co-expressing recombinant furin. FEBS Lett 1995; 375: 259-262).

In particular, when plasma fractions are used, a pH precipitation can be carried out prior to the hydroxylapatite chromatography to separate fibronectin. The pH precipitation serving for separating fibronectin from a plasma fraction comprises e.g. that (i) the pH value of the plasma fraction is adjusted to below pH 5.4 so as to form a precipitate, and
(ii) the precipitate formed is separated.

The expression "plasma fraction" refers in this connection to a composition which was obtained from plasma and contains various plasma proteins. The plasma fraction which is used as a starting composition in step (i), is a liquid composition. Preferably, the liquid composition is a solution or a suspension, most preferably the composition is a solution. In a particular embodiment, the plasma fraction is dissolved cryoprecipitate. This dissolved cryoprecipitate can be previously purified by various processes. Examples are aluminum hydroxide treatment, solvent/detergent treatment and/or anion exchange chromatography. The concentration of sodium chloride or potassium chloride in the plasma fraction is preferably 50 to 250 mM, more preferably 100 to 200 mM, most preferably 120 to 150 mM. The plasma fraction may contain e.g. the following buffer substances: citrate ions, acetate ions, phosphate ions and/or amino acids.

The fibronectin concentration in the plasma fraction, which is subjected to step (i), is usually at least 0.05 g/l, preferably at least 0.1 g/l, more preferably at least 0.25 g/l, most preferably at least 0.5 g/l. The fibronectin concentration in the plasma fraction can be 0.1 to 5 g/l, preferably 0.1 to 2 g/l, for example.

In order to separate fibronectin from the plasma fraction, the pH value of the plasma fraction is adjusted below pH 5.4. In this connection, a precipitate forms which contains fibronectin. Preferably, the pH is adjusted to below pH 5.3, more preferably to below pH 5.2. The adjusted pH is thus preferably within a range of pH 4.5 to below 5.4, preferably within a range of pH 4.7 to 5.3, more preferably within a range of pH 4.8 to 5.2, even more preferably within a range of pH 4.9 to 5.1. The adjustment of the pH is usually achieved by adding an acidic component. Various acids may be used as the acidic component, e.g. hydrochloric acid, phosphoric acid or acetic acid. The acidic component is usually added over a certain period of time, e.g. drop-wise. Thus, a pH within the range defined above in more detail is gradually adjusted ("titrated").

During and after the pH adjustment, the plasma fraction is preferably kept moving or mixed, e.g. by stirring. It is also preferred that after the pH adjustment the plasma fraction is further mixed for a certain period of time (e.g. by stirring), in general for at least 10 minutes, preferably for at least 20 minutes, most preferably for a period of 30 to 90 minutes. During this period, sticky aggregates form which have a considerable fibronectin content. Therefore, according to a preferred embodiment a suitable stirrer, e.g. an anchor agitator or paddle mixer, shall be used to the agitator blade of which the precipitate adheres. Thus, the precipitated fibronectin can easily be removed from the solution.

The pH precipitation of fibronectin can be carried out within a wide temperature spectrum, e.g. from about 1° C. to about 37° C. Preferred temperature ranges are 4 to 35° C., more preferably 10 to 30° C., most preferably the process is carried out from 20 to 25° C.

The fibronectin concentration in the plasma fraction can be reduced by at least 50% by pH precipitation to separate fibronectin from plasma fractions. The fibronectin concentration in the plasma fraction is preferably reduced by 70 to 99%, more preferably by 80 to 99%, most preferably by 90 to 98% or by 95 to 98%. In a particular embodiment, the loss of VWF in the precipitation step is at most 50%, preferably at most 40%, more preferably at most 30%, even more preferably at most 20%, most preferably at most 10%.

A further aspect of the present invention is a VWF containing composition which can be obtained by a process according to the invention as described in this application. Preferably it is a substantially pure VWF preparation. "Substantially pure" means that the protein content of the composition is at least 70% VWF molecules.

By means of the process according to the invention it is possible to achieve specific activities of >60 U per mg protein without fine purification and of >100 U per mg protein with a fine purification. The protein solution can then be rebuffered and lyophilized. Further virus inactivation steps, such as the incubation of the lyophilizate at 100° C. for 30 minutes, are also possible, where appropriate.

Hydroxylapatite, in particular in its ceramic stabilized form, is extremely well suited to carry out processes on an industrial scale. For example, it can be used for the separation of fibronectin from VWF containing plasma fractions in a much more cost effective and reproducible way than e.g. gelatin sepharose or other affinity chromatography media. On account of its separating characteristics, hydroxylapatite offers a better resolution than the frequently described ion exchange chromatography media. In the hydroxylapatite purification method, neither calcium nor amino acids have to be added to the buffers.

Since hydroxylapatite permits substantially higher flow rates and longer service lives than frequently used affinity chromatography media, an extremely economical production process for a highly pure VWF preparation is provided by this method. The excellent sanitary capacity of the material with e.g. 1 M NaOH additionally results in optimum product safety.

The various embodiments described in this application may be combined.

The below examples explain the invention in more detail.

EXAMPLE 1

Purification of a VWF Containing Plasma Fraction by Means of Hydroxylapatite Flow Chromatography The VWF containing protein solution passed through the following preliminary purification steps, as described in WO 9315105 A1, for example: A cryoprecipitate solution was subjected to an aluminum hydroxide precipitation. Thereafter, a virus inactivation was carried out by means of S/D treatment. In the then following anion exchange chromatography, a VWF containing wash fraction was obtained which was above all contaminated with fibrinogen and fibronectin. By titration to pH 5.2, the protein solution was subjected to a precipitation step where the majority of fibronectin and fibrinogen were removed. Thereafter, ultrafiltration and diafiltration were carried out, the protein solution being concentrated about 7 times and diafiltrated against the running buffer of the following chromatography. The resulting protein solution contained about 930 µg/ml VWF antigen, 270 µg/ml fibrinogen antigen and 2400 µg/ml fibronectin antigen. The protein solution was applied onto a hydroxylapatite column equilibrated in 10 mM Na phosphate, pH 7.0 (CHT type 1, Bio-Rad, Munich, Germany). The flow fraction contained about 560 µg/ml VWF antigen, 5 µg/ml fibrinogen antigen, and 50 µg/ml fibronectin antigen. The mass balance results in a step yield of 78% for the VWF antigen. On account of the very good purification effectiveness, the yield has to be regarded as excellent.

TABLE 2

Purification of a VWF containing plasma fraction
by means of hydroxylapatite flow chromatography

|  | VWF antigen | Fibrinogen antigen | Fibronectin antigen | Yield |
|---|---|---|---|---|
| stock | 930 µg/ml | 270 µg/ml | 2400 µg/ml |  |
| Flow fraction | 560 µg/ml | 5 µg/ml | 50 µg/ml | 78% |

The WVF antigen concentration was determined by means of the STA® Compact of Diagnostic Stago company (Roche Diagnostics, Mannheim, Germany) and its test reagents (STA LIA vWF).

In order to determine the amount of fibrinogen antigen and fibronectin antigen, nephelometric methods were used to quantitatively determine the fibrinogen antigen and fibrinogen antigen concentration in the Beckman-Arraye® 360 (Beckman Coulter, Monheim, Germany).

EXAMPLE 2

Fine Purification Using a Binding Hydroxylapatite Chromatography

A protein solution produced according to that of Example 1 was titrated to pH 6.0 for further purification. Thereafter, the solution was applied onto a hydroxylapatite column (CHT type 1, Bio-Rad, Munich, Germany) which had been equilibrated in the running buffer (20 mM sodium phosphate, pH 6.0). The VWF was bound quantitatively. A first elution was carried out with 230 mM sodium phosphate, pH 6.0, the second with 400 mM sodium phosphate, pH 6.0. The applied protein solution contained 540 µg/ml VWF antigen, 4 µg/ml fibrinogen, and 48 µg/ml fibronectin. The first elution fraction contained 38 µg/ml VWF antigen, 2 µg/ml fibronectin antigen. The fibrinogen antigen concentration was below the detection limit of 1 µg/ml. The fraction of interest ($2^{nd}$ elution fraction) had a VWF antigen concentration of 173 µg/ml. Neither fibrinogen antigen nor fibronectin antigen could be detected. The VWF activity was 23 U/ml, the entire protein concentration ($OD_{280nm}$) was 0.23 mg/ml. A specific activity of 100 U/mg protein was obtained.

TABLE 3

Fine purification using a binding hydroxylapatite chromatography

|  | VWF antigen | Fibrinogen antigen | Fibronectin antigen | Specific activity |
|---|---|---|---|---|
| Stock | 540 µg/ml | 4 µg/ml | 48 µg/ml | 56 U/mg |
| Elution fraction 1 | 38 µg/ml | Not defined | 2 µg/ml | 12 U/mg |
| Elution fraction 2 | 173 µg/ml | Not defined | Not defined | 100 U/mg |

The VWF activity was determined as ristocetin cofactor activity via platelet agglutination using the BCT® Analyzer (Behring Coagulation Timer, Dade Behring, Schwalbach, Germany).

The protein was determined according to the Lambert Beer law ($A = \epsilon \cdot c \cdot d$), wherein
A=absorption at 280 nm
$\epsilon$=coefficient of absorption (here theoretical coefficient of absorption 0.75 cm$^2$/mg)
c=protein concentration in mg/ml
d=layer thickness in cm.

EXAMPLE 3

Increase in the Specific Activity of a Previously Purified VWF Containing Plasma Fraction by Means of Binding Fluoroapatite Chromatography The initial solution was prepared in accordance with Example 1. The protein solution contained a specific activity of 64.8 U/mg at a protein concentration of 0.83 mg/ml.

The protein solution was titrated to a pH value of 6.0 by the addition of HCl. Thereafter, the solution was applied onto a fluoroapatite column (CFT type 1, Bio-Rad, Munich, Germany) with a gel bed volume of 13.2 ml, which had been equilibrated in the running buffer (20 mM Na phosphate, pH 6.0). Part of VWF was bound. A separation of impurities was obtained by a first elution with a buffer containing 241 mM Na phosphate, pH 6.0 (elution fraction 1). The fraction of interest was then eluted with 400 mM Na phosphate, pH 6.0. By this chromatographic step, the specific activity could be raised to 77.0 U/mg protein. On account of the weaker binding of VWF under the chosen pH conditions, no complete binding of VWF occurs so that part is in the flow fraction.

TABLE 4

Increase in the specific VWF activity of a previously purified VWF containing plasma fraction by means of fluoroapatite chromatography

|  | Specific activity [U per mg protein] |
|---|---|
| Stock | 64.8 |
| Flow | 47.1 |
| Elution fraction 1 | 39.3 |
| Fraction of interest | 77.0 |

Additional Citations

The following citations are mentioned additionally in connection with various analytical methods.

VWF Activity:

Veyradier A, Fressinaud E, Meyer D (1998): Laboratory diagnosis of von Willebrand disease. Int J Lab Res 28 (4): 201-210.

VWF Antigen:

Budde U, et al. (1984): Acquired von Willebrand's disease in the myeloproliferative syndrome. Blood 64 (5): 981-985.

Newman D J, Henneberry H, Price C P (1992): Particle enhanced light scattering immunoassay. Ann Clin Biochem 29 (Pt1): 22-42.

Fibronectin Antigen:

Sandberg L, et al. (1985): Plasma fibronectin levels in acute and recovering malnourished children. Clin Physiol. Biochem. 3(5):257-264.

Colli A, et al. (1986): Diagnostic accuracy of fibronectin in the differential diagnosis of ascites. Cancer: 58(11):2489-2493.

Fibrinogen Antigen:

Ernst E, Resch K L (1993): Fibrinogen as a cardiovascular risk factor: a meta-analysis and review of the literature. Ann Intern Med.: 118(12):956-963.

Jelic-Ivanovic Z, Pevcevic N (1990): Fibrinogen determination by five methods in patients receiving streptokinase therapy. Clin Chem.: 36(4):698-699.

The invention claimed is:

1. A process for purifying wild-type von Willebrand factor (VWF) from a plasma fraction comprising steps of:
    (i) providing a sample of plasma fraction containing wild-type VWF and one or more contaminating proteins comprising fibronectin and/or fibrinogen;
    (ii) preparing the sample of plasma fraction in a first running buffer at pH of 7.0-7.5 that consists essentially of 10-50 mM sodium and/or potassium phosphate,
    (iii) performing flow chromatography by loading the sample of plasma fraction to a hydroxylapatite matrix under conditions that 90% or more of fibronectin and/or fibrinogen bind to the hydroxylapatite matrix, while at the same time, less than 10% of the wild-type VWF bind to the hydroxylapatite matrix thereby providing a flow through fraction(s) containing purified wild-type VWF, wherein the flow chromatography is performed with the first running buffer; and
    (iv) purifying wild-type VWF by collecting unbound wild-type VWF from the flow through fraction(s).

2. The process according to claim 1, further comprising step of:
    (v) performing binding chromatography by loading the purified wild-type VWF to hydroxylapatite matrix under a condition such that the wild-type VWF is bound to a hydroxylapatite matrix and then subsequently eluted, wherein the flow chromatography is performed with a second running buffer at pH 5.5-6.8.

3. The process according to claim 2, wherein the step (v) comprises: (a) binding the wild-type VWF to the hydroxylapatite matrix, (b) washing out impurities, and (c) eluting the wild-type VWF thereby further purifying the wild-type VWF.

4. The process according to claim 3, wherein the step (a) is performed by the second running buffer with 1 to 200 mM sodium and/or potassium phosphate.

5. The process according to claim 3, wherein the step (b) is performed by the second running buffer with 100 to 300 mM sodium and/or potassium phosphate.

6. The process according to claim 3, wherein the step (c) is performed with the second running buffer with 200 to 500 mM sodium and/or potassium phosphate.

7. The process according to claim 1, wherein the sample of plasma fraction in step (i) has been previously purified.

8. The process according to claim 1, wherein the sample of plasma fraction in step (i) comprises a separately purified cryoprecipitate solution.

9. The process according to claim 1, wherein the sample of plasma fraction in step (i) comprises a cryoprecipitate solution precipitated with aluminum hydroxide.

10. The process according to claim 1, wherein the sample plasma fraction in step (i) comprises a chromatographically pre-purified cryoprecipitate solution precipitated with aluminum hydroxide.

11. The process according to claim 1, further comprising the step of performing a pH precipitation prior to step of carrying out flow chromatography with hydroxylapatite matrix to separate fibronectin.

12. The process according to claim 1, wherein the hydroxylapatite is fluoroapatite.

* * * * *

UNITED STATES PATENT AND TRADEMARK OFFICE
CERTIFICATE OF CORRECTION

PATENT NO. : 7,939,643 B2  
APPLICATION NO. : 10/594455  
DATED : May 10, 2011  
INVENTOR(S) : Michael Kretschmar et al.

Page 1 of 1

It is certified that error appears in the above-identified patent and that said Letters Patent is hereby corrected as shown below:

In the Claims

On column 11, line 28 (claim 2, line 7), please replace the word "flow" with -- binding --.

Signed and Sealed this
Twenty-first Day of May, 2013

Teresa Stanek Rea
*Acting Director of the United States Patent and Trademark Office*